US012745985B2

(12) United States Patent
Huang et al.

(10) Patent No.: US 12,745,985 B2
(45) Date of Patent: Sep. 29, 2026

(54) BIOLOGICAL TISSUE ELASTICITY DIMENSIONAL DETECTION METHOD AND DETECTION SYSTEM, AND STORAGE MEDIUM

(71) Applicant: EIELING TECHNOLOGY LIMITED, Hong Kong (HK)

(72) Inventors: Zihao Huang, Hong Kong (HK); Like Wang, Hong Kong (HK); Yongping Zheng, Hong Kong (HK)

(73) Assignee: EIELING TECHNOLOGY LIMITED, Hong Kong (HK)

( * ) Notice: Subject to any disclaimer, the term of this patent is extended or adjusted under 35 U.S.C. 154(b) by 248 days.

(21) Appl. No.: 18/014,489

(22) PCT Filed: Jun. 30, 2021

(86) PCT No.: PCT/CN2021/103784
§ 371 (c)(1),
(2) Date: Jan. 5, 2023

(87) PCT Pub. No.: WO2022/007687
PCT Pub. Date: Jan. 13, 2022

(65) Prior Publication Data
US 2023/0255600 A1 Aug. 17, 2023

(30) Foreign Application Priority Data
Jul. 7, 2020 (CN) ......................... 202010644961.1

(51) Int. Cl.
*A61B 8/00* (2006.01)

(52) U.S. Cl.
CPC .............. *A61B 8/485* (2013.01); *A61B 8/463* (2013.01); *A61B 8/483* (2013.01)

(58) Field of Classification Search
None
See application file for complete search history.

(56) References Cited

U.S. PATENT DOCUMENTS

2008/0081994 A1* 4/2008 Kim ..................... A61B 5/0285 600/438
2012/0123263 A1* 5/2012 Osaka .................. A61B 5/0051 600/438
(Continued)

FOREIGN PATENT DOCUMENTS

CN 101150990 A 3/2008
CN 101843501 A 9/2010
CN 104640506 A 5/2015

OTHER PUBLICATIONS

Zeng, Qi, et al. "3D liver shear wave absolute vibro-elastography with an xMATRIX Array—a healthy volunteer study." 2018 IEEE International Ultrasonics Symposium (IUS). IEEE, 2018. (Year: 2018).*
(Continued)

*Primary Examiner* — Christopher Koharski
*Assistant Examiner* — Renee C Langhals

(57) ABSTRACT

A biological tissue elasticity dimensional detection method and detection system, and a storage medium. The detection method comprises: using an ultrasonic transducer array to acquiring an ultrasonic image of a target object, establishing a coordinate system of a sampling region of interest, and determining the number of sampling points and coordinate distribution positions thereof; in response to an external vibration excitation, collecting multiple elastic feature parameters at a designated coordinate position, and reconstructing a parameter value that contains spatial position information and a corresponding ultrasonic image, and comprising the synthesis, superimposition and fusion of maps, and simultaneously displaying. Multiple elastic feature parameters within a certain range can be measured by means of a single detection point, not only improving detection efficiency, but also minimizing sampling errors.

7 Claims, 6 Drawing Sheets

(56) References Cited

U.S. PATENT DOCUMENTS

| | | | | |
|---|---|---|---|---|
| 2014/0243668 | A1* | 8/2014 | Varghese ............ | G01S 7/52042 600/438 |
| 2016/0143621 | A1 | 5/2016 | Parthasarathy et al. | |
| 2019/0244352 | A1 | 8/2019 | Honjo et al. | |
| 2019/0328364 | A1* | 10/2019 | Questa ................ | G01S 7/52042 |
| 2019/0357886 | A1 | 11/2019 | Cao et al. | |

OTHER PUBLICATIONS

International Search Report of PCT Patent Application No. PCT/CN2021/103784 issued on Sep. 28, 2021.

European Search Report of European Patent Application No. 21838931.0 issued on Jun. 18, 2024.

Zeng Qi et al.: "3D Liver Shear Wave Absolute Vibro-Elastography with an xMATRIX Array—A Healthy Volunteer Study", 2018 IEEE International Ultrasonics Symposium (IUS), IEEE, Oct. 22, 2018, XP033479919.

* cited by examiner

S100B the step of acquiring ultrasonic image of the target object: acquiring B-mode ultrasonic images, guiding the positioning of liver tissues; in the selected B-mode ultrasonic image, determining the number of sampling points in the region of interest of the target object; in the selected B-mode ultrasonic image, determining the distribution pattern of sampling points in the region of interest based on the number of selected sampling points the steps of collecting 3D data and mapping to generate 3D elastic mapping: triggering the generation and propagation of shear waves; measuring multiple elastic feature parameters on each sampling point including longitudinal depth, transverse length and thickness in the region of interest; post-processing the corresponding elastic feature parameters measured at each sampling point, and constructing a three-dimensional elastic mapping map by interpolation, fitting and other mathematical processing methods for the processed elastic feature parameters

S200B the steps of fusing and displaying: superpose and fuse the elastic map containing three-dimensional elastic distribution data into the B-mode ultrasonic image and display it synchronously

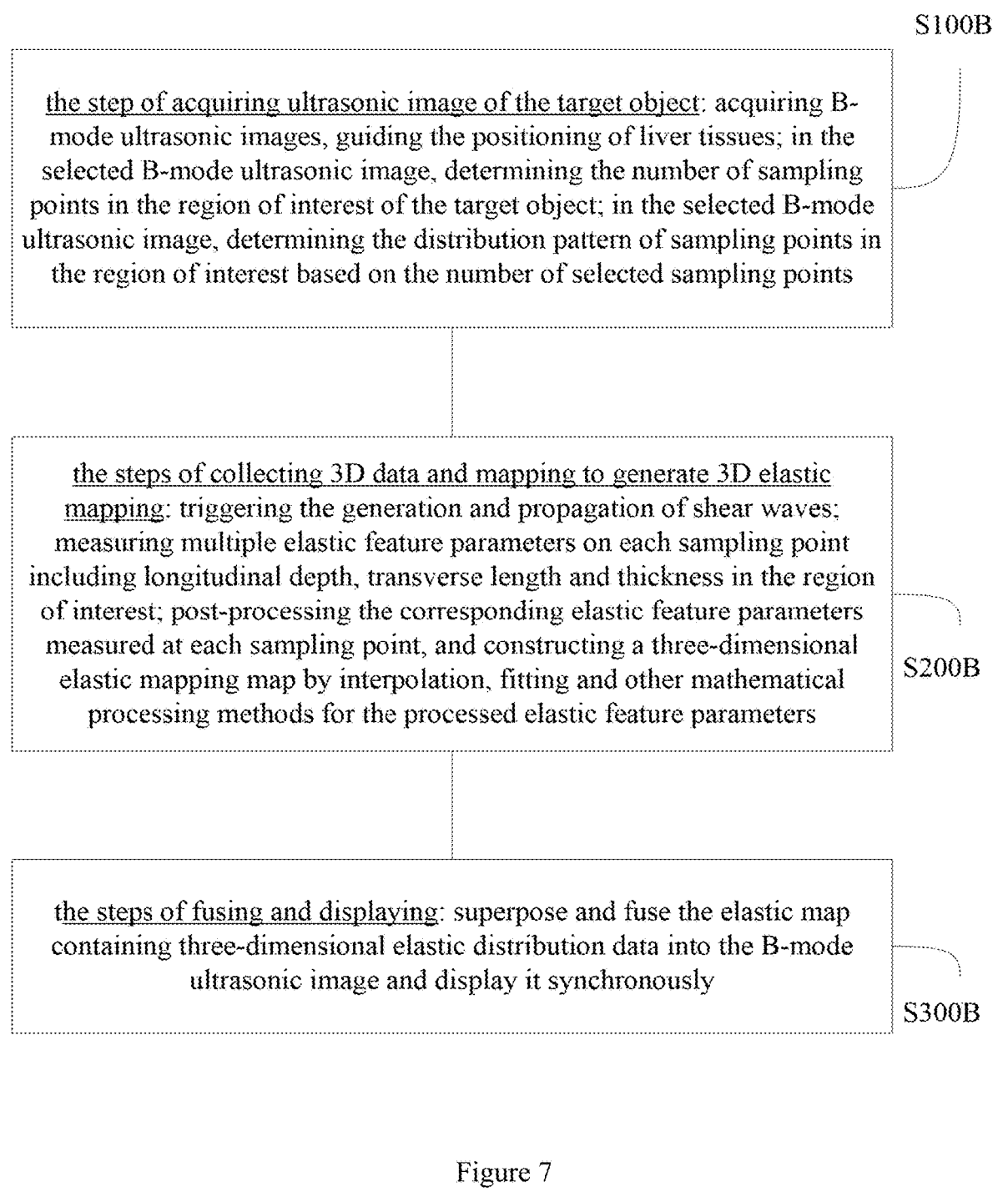

S300B

Figure 7

BIOLOGICAL TISSUE ELASTICITY DIMENSIONAL DETECTION METHOD AND DETECTION SYSTEM, AND STORAGE MEDIUM

TECHNICAL FIELD

The present application relates to the technical field of ultrasonic diagnosis, in particular to a biological tissue elasticity dimensional detection method and detection system, and a storage medium.

BACKGROUND

Some liver diseases may result in non-extensive distribution of fibrosis and uneven hardness of liver parenchyma. In this regard, the existing elastic imaging and measurement technologies of biological tissues include Transient elastography, Ultrasonic shear imaging, ARFI elastography and Strain elastography. Generally, the transient elasticity measurement method is a technology that uses pulse vibration and then measures shear wave propagation for elasticity measurement and imaging. Among them, the transient elastic detection technology using external vibration to generate shear wave propagation in the liver is a relatively simple and low-cost scheme, so it is widely used in clinical. However, the existing liver transient elasticity detection technology can only do single value measurement, that is, a fixed-depth sampling strategy is used, and only scalars are measured (only with numerical size, but no dimension). To acquire a dimensional elastic distribution in the liver, it can only be achieved by artificially moving the probe at the detection point on the body surface, so this method is time-consuming and labor-intensive. At present, according to the above existing liver transient elasticity detection technology, the widely accepted inspection scheme is to quantify the degree of liver fibrosis of the examinee by multiple effective single value measurements and calculating the median. However, similar schemes lead to low inspection efficiency, and the reliability and repeatability of results are greatly affected by operators.

The disadvantage of the single-value elastic measurement technique is that only single-sample can be done and there are sampling errors (i.e., cannot obtain spatial distribution information). In the prior art (Publication No. CN101843501A), there are methods and instruments for calculating elastic parameters through B-mode ultrasound imaging and constructed transient M-mode images, but they do not describe a specific solution for realizing an elasticity dimensional detection. However, an elasticity dimensional detection can more intuitively display the spatial distribution of elasticity, which has clinical significance for the diagnosis and monitoring of lesions.

SUMMARY

Aiming at the problems of sampling errors and low detection reliability in the prior art, the present application provides an elasticity dimensional detection that uses an ultrasonic transducer array to realize an elasticity detection method, detection system and storage medium with low a sampling error rate.

The technical scheme of the present application for the above technical problems is as follows:

the present application provides an elasticity dimensional detection method for biological tissue detection, wherein, the method comprises the following steps: acquiring an ultrasonic image of a target object; in response to an external vibration excitation, collecting elastic feature parameters at a designated coordinate position of the target object, and mapping to generate an elastic map; superimposing and fusing the elastic map containing elastic distribution data to the ultrasonic image and simultaneously displaying.

According to the above method, the ultrasonic image used to locate a position of the target object is a two-dimensional ultrasonic image containing an anatomical structure information of the target object; based on the ultrasonic image, establishing a coordinate system of a sampling region of interest, and determining the number of sampling points and coordinate distribution positions thereof; the region of interest is located in a selected ultrasonic image and is one of the coordinate systems of uniaxial linear direction, two-dimensional plane or three-dimensional space; based on the coordinate system dimension and position of the selected region of interest, the sampling points are specific coordinate points located in the coordinate system, which can be distributed according to specific positions.

According to the above method, the step of collecting elastic feature parameters at a designated coordinate position of the target object, and mapping to generate an elastic map comprising: measuring elastic feature parameters of the sampling points of the target object: stimulating the probe to apply low-frequency mechanical vibration on body surface and generate shear wave to propagate in biological tissues; controlling the array elements in the ultrasonic transducer array to transmit and receive ultra-high frame rate ultrasonic tracking shear wave along the designated coordinate position or different directions of each sampling point, and performing parameter measurements on multiple sampling points simultaneously or with mutually delay; mapping to generate the elastic map: using mapping technology to encode the elastic feature parameters at the designated coordinate position into single value mapping map or color mapping map to represent the distribution state of elastic features; the elastic feature parameters are parameters related to the elasticity of biological tissues, including elastic parameters expressed by Young's modulus, ultrasonic parameters, and two-dimensional ultrasonic image feature parameters.

According to the above method, triggering the probe to transmit directional ultra-high frame rate ultrasound signal to track the shear wave for sampling, and calculating the time delay of transmitting and receiving the ultrasonic wave for corresponding array elements in the transducer array before sampling; the sampling mode includes: obtaining a radio frequency (RF) signal by stimulating a single array element of the probe, and calculating the elastic feature parameters at a designated position in a single dimensional space; or obtaining the radio frequency (RF) signal by controlling different array elements of the probe in parallel, and calculating the elastic feature parameters at the designated position in the multi-dimensional space.

According to the above method, the elasticity dimensional detection method comprises one-dimensional, two-dimensional and three-dimensional ultrasonic transient elasticity detection, specifically including processing steps: acquiring the two-dimensional ultrasonic image, determining the position of the region of interest on the two-dimensional ultrasonic image; and establishing the sampling coordinate system of the corresponding dimension in the region of interest, and determining the number of and coordinate position of the sampling points in the selected corresponding dimension sampling coordinate system; measuring at least one elastic feature parameter on each selected sampling point in the region of interest through a probe; mapping and processing corresponding elastic feature parameters measured at each sampling point to construct an elastic map of the sampling coordinate system of the corresponding dimension; superimposing and fusing the elastic map of corresponding dimensions to the two-dimensional ultrasonic image and displaying it simultaneously.

According to the above method, the collecting of the three-dimensional data of the three-dimensional ultrasound transient elasticity detection is realized by single point detection in which a two-dimensional array probe is fixedly placed on a single detection point on the body surface; or by multi-point detection in which a linear probe, a phased probe or a convex array probe are moved on multiple detection points on the body surface.

According to the above method, the external vibration excitation is continuously applied at a certain repetition rate, and the ultra-high frame rate ultrasound simultaneously tracks the propagation of multiple shear waves generated in the biological tissue by continuous vibration.

According to the above method, the collecting of the ultra-high frame rate ultrasound is carried out simultaneously at least two positions or directions.

The present application also provides an elasticity dimensional detection system for biological tissue detection, comprises an image acquiring unit for acquiring an ultrasonic image of a target object and a probe for transmitting and receiving ultrasonic wave signal; wherein, the detection system further comprises: a main control unit, respectively connected with the image acquiring unit and the probe, is used to acquire ultrasonic image of the target object, establish a coordinate system of a sampling region of interest of a corresponding dimension, and determine a number of sampling points and coordinate distribution positions thereof; receive the elastic feature parameters of the corresponding region of interest of the target object, map to generate an elastic map, and superimpose and fuse the elastic map containing elastic distribution data to the ultrasonic image and display it synchronously.

According to the above system, the probe comprises an ultrasonic probe and a low-frequency vibrator coupled with the ultrasonic probe; the ultrasonic probe is arranged by several ultrasonic piezoelectric transducer array elements in a linear, convex or two-dimensional array; the low-frequency vibrator continuously applies mechanical vibration on the body surface at a certain repetition rate to generate a plurality of shear waves propagated in biological tissues by continuous vibration.

According to the above system, the main control unit comprises a control unit and a processing unit, the control unit is respectively connected with the image acquiring unit, the probe and the processing unit, the control unit is used to receive the ultrasonic image of the image acquiring unit and transmit the ultrasonic image to the processing unit; the processing unit is used to determine the distribution coordinates of the sampling points in the region of interest according to the ultrasonic image, and transmit the distribution coordinate information of the sampling points to the control unit; the control unit is also used to control the low-frequency vibrator to send shear waves to the target object according to the distribution coordinates of the sampling points, and send ultra-high frame rate ultrasound signals to the distribution coordinates of the sampling points with the ultrasonic transducer array elements of the probe, and receive RF signals fed back by the distribution coordinates of the sampling points; and transmit the RF signal obtained by the probe and its distribution data to the processing unit; the processing unit is also used to calculate the corresponding elastic feature parameters according to the received RF signal of each coordinate and its distribution data, establish a single dimensional or multi-dimensional state elastic map, and fuse the corresponding map with the ultrasonic image; the fused image is synchronously displayed by a display unit connected with the processing unit.

A third aspect of the present application provides a computer-readable storage medium, storing computer programs, when the computer programs are executed by the CPU in the main control unit, the following steps are realized by the CPU: acquiring an ultrasonic image of a target object; in response to an external vibration excitation, collecting elastic feature parameters at a designated coordinate position of the target object, and mapping to generate an elastic map; superimposing and fusing the elastic map containing elastic distribution data to the ultrasonic image and simultaneously displaying.

The technical scheme provided by the embodiment of the present application has the following beneficial effects:

Aiming at the limitation that the single-value elastic measurement technology in the prior art can only realize a single sample at one time and cannot obtain spatial distribution information, the present application provides a detection method that can realize multiple sampling, that is, simultaneously measure multiple elastic feature parameters and synthesize the elastic distribution map by single detection at a detection point without manually moving the position of the probe; by controlling the corresponding array elements in the ultrasonic transducer array to transmit and receive ultra-high frame rate ultrasound, obtaining elastic feature parameters with multiple spatial distributions and mapping them to generate single value mapping map or color elastic mapping map; processing the elastic map containing elastic distribution data, superposing and fusing them to the ultrasonic image to visualize the spatial distribution state of elastic features of biological tissues; the present application can measure multiple elastic feature parameters within a certain range through a single detection point, which not only improves the detection efficiency, but also saves time; the increase of sample size minimizes the system error and improves the reliability of the results; the sampling error is reduced; an adjustable and switchable sampling point distribution mode is provided, which can selectively avoid the large blood vessels and bile duct system, obtain the distribution status of biological parameters of biological tissues, and make the results more accurate and customized.

BRIEF DESCRIPTION OF THE DRAWINGS

FIG. 7 is a flow diagram of the three-dimensional ultrasonic transient elasticity detection provided by the first embodiment of the present application.

DETAILED DESCRIPTION OF THE PREFERRED EMBODIMENT

In order to solve the technical problems in the prior art, such as high sampling error rate, low inspection efficiency and low reliability of results, the present application aims to provide a biological tissue elasticity dimensional detection method using an ultrasonic transducer array. Its core idea is: using an ultrasonic transducer array to an ultrasonic image of a target object, establishing a coordinate system of a sampling region of interest, and determining the number of sampling points and coordinate distribution positions thereof; in response to an external vibration excitation, collecting multiple elastic feature parameters at a designated coordinate position, and reconstructing a parameter value that contains spatial position information and a corresponding ultrasonic image, and comprising the synthesis, superimposition and fusion of maps, and simultaneously displaying, and obtaining one-dimensional, two-dimensional and three-dimensional elastic distribution of biological tissue; in a dimensional elasticity detection system adopted by the detection method of the present application, by controlling corresponding array elements in a transducer array to transmit and receive ultra-high frame rate ultrasound and by post-processing RF signals and images, the spatial distribution state of elastic features within biological tissue can be visualized. The low-frequency vibrator emits low-frequency vibration to the target object to generate shear wave; the ultrasonic probe transmits and receives ultrasonic waves to and from the target object to obtain ultrasonic images, and receives RF signals fed back from the distribution coordinates of the sampling points of the target object; the processing unit in the system receives the RF signal and its distribution data of the region of interest of the target object, maps and generates the one-dimensional, two-dimensional or three-dimensional elastic mapping map of the target object, and superimposes and fuses the elastic mapping map containing the elastic distribution data to the ultrasonic image and displays it synchronously through the display unit. Multiple elastic feature parameters within a certain range can be measured by means of a single detection point, not only improving detection efficiency, but also minimizing sampling errors.

In order to make the purpose, technical scheme and advantages of the present application clearer, the embodiments of the present application will be further described in detail in combination with the accompanying drawings.

Figure 1:
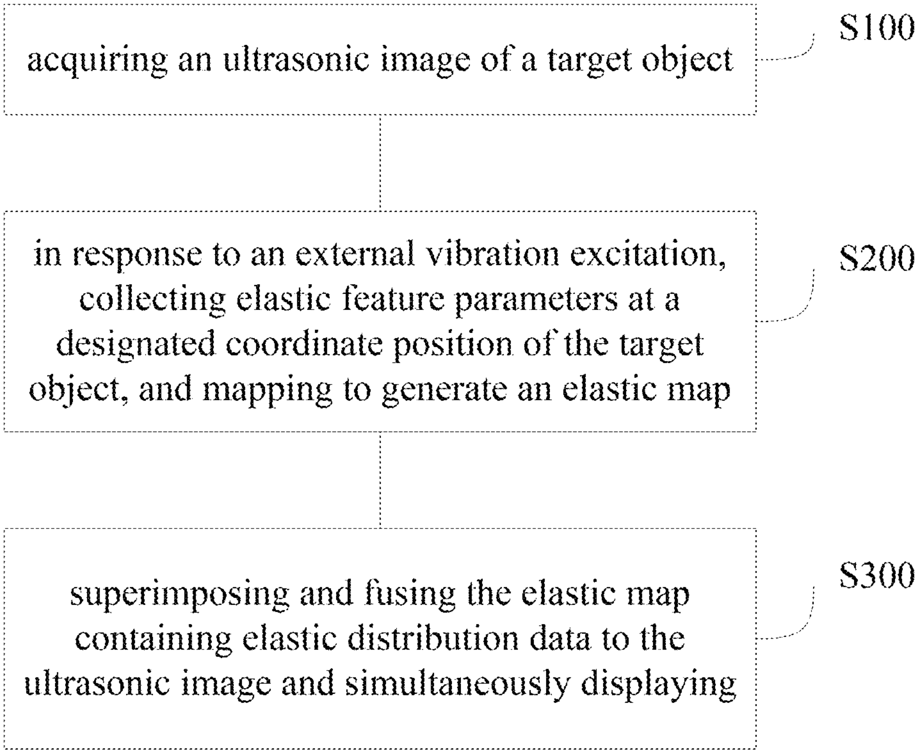
FIG. 1 is a flow diagram of the biological tissue elasticity dimensional detection method provided by the first embodiment of the present application.

A flow diagram of a biological tissue elasticity dimensional detection method (in this embodiment, the selected biological tissue is the liver) is provided in the first embodiment of the present application. As shown in FIG. 1, the method mainly includes the following processing steps:

S100. acquiring an ultrasonic image of a target object.

Wherein, the ultrasonic transducer is used to transmit the ultrasound and receive the echo signal reflected by the liver to obtain the morphological image of the liver. At the same time, the region of interest of the target object is confirmed and a coordinate system of a sampling region of interest is established, and the number of sampling points and coordinate distribution positions are determined. The morphological images of the target object include two-dimensional ultrasonic images containing liver anatomical structure information, including B-mode ultrasonic images, color and power Doppler images, etc.

S200. in response to an external vibration excitation, collecting elastic feature parameters at a designated coordinate position of the target object, and mapping to generate an elastic map.

It specifically includes the following steps: measuring elastic feature parameters of the sampling points of the target object and mapping to generate the elastic map. Wherein measuring elastic feature parameters of the sampling points of the target object: stimulating the probe to apply low-frequency mechanical vibration on body surface and generate shear wave to propagate in biological tissues; controlling the array elements in the ultrasonic transducer array to transmit and receive ultra-high frame rate ultrasonic tracking shear wave along the designated coordinate position or different directions of each sampling point, and performing parameter measurements on multiple sampling points simultaneously or with mutually delay; the collecting of the ultra-high frame rate ultrasound is carried out simultaneously at least two positions or directions; the elastic feature parameters are parameters related to the elasticity of the liver, including elastic parameters expressed by Young's modulus, ultrasonic parameters, and two-dimensional ultrasonic image feature parameter. Mapping to generate the elastic map: using mapping technology to encode the elastic feature parameters at the designated coordinate position into single value mapping map or color mapping map to represent the distribution state of elastic feature. The mapping map can be a one-dimensional, two-dimensional or three-dimensional image.

S300. superimposing and fusing the elastic map containing elastic distribution data to the ultrasonic image and simultaneously displaying.

The above detection method includes one-dimensional, two-dimensional and three-dimensional ultrasonic transient elasticity detection, and further includes processing steps: acquiring the two-dimensional ultrasonic image, determining the position of the region of interest on the two-dimensional ultrasonic image; and establishing the sampling coordinate system of the corresponding dimension in the region of interest, and determining the number of and coordinate position of the sampling points in the selected corresponding dimension sampling coordinate system; measuring at least one elastic feature parameter on each selected sampling point in the region of interest through a probe; mapping and processing corresponding elastic feature parameters measured at each sampling point to construct an elastic map of the sampling coordinate system of the corresponding dimension; superimposing and fusing the elastic map of corresponding dimensions to the two-dimensional ultrasonic image and displaying it simultaneously.

The collecting of the three-dimensional data of the three-dimensional ultrasound transient elasticity detection is realized by single point detection in which a two-dimensional array probe is fixedly placed on a single detection point on the body surface; or by multi-point detection in which a linear probe, a phased probe or a convex array probe are moved on multiple detection points on the body surface.

Wherein, triggering the probe to transmit directional ultra-high frame rate ultrasound signal to track the shear wave for sampling, and calculating the time delay of transmitting and receiving the ultrasonic wave for corresponding array elements in the transducer array before sampling. The time delay refers to the back scattering or reflected wave received by the transducer array element due to the scattering and reflection of the tissue during the propagation of the ultrasonic wave in the tissue. The time of receiving the signal corresponds to the depth position of the sampling point one by one, so by controlling the time delay of the reception relative to the transmission, the ultrasonic signal of the specified depth and direction can be selectively received. Further, the sampling mode includes: obtaining a radio frequency (RF) signal by stimulating a single array element of the probe, and calculating the elastic feature parameters at a designated position in a single dimensional space; or obtaining the radio frequency (RF) signal by controlling different array elements of the probe in parallel, and calculating the elastic feature parameters at the designated position in the multi-dimensional space.

Figure 2:
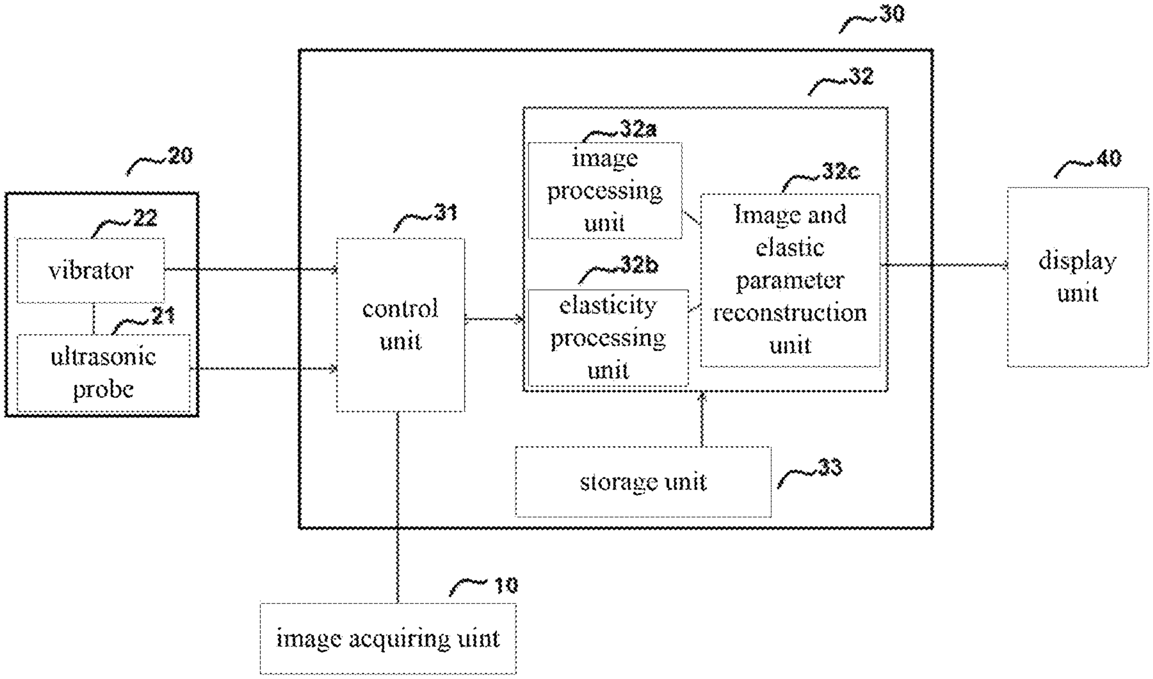
FIG. 2 is the block diagram of the biological tissue elasticity dimensional detection system provided by the second embodiment of the present application.

In combination with the elasticity dimensional detection system of the second embodiment provided in FIG. 2, the system is applied to the detection method for biological tissues in the first embodiment (in this embodiment, the selected biological tissues are liver). The elasticity dimensional detection system comprises an image acquiring unit 10 for acquiring an ultrasonic image of a target object and a probe 20 for transmitting and receiving ultrasonic wave signal; wherein, the detection system further comprises a main control unit 30 respectively connected with the image acquiring unit 10 and the probe 20 and a display unit 40. The main control unit 30 is used to acquire ultrasonic image of the target object, establish a coordinate system of a sampling region of interest of a corresponding dimension, and determine a number of sampling points and coordinate distribution positions thereof; receive the elastic feature parameters of the corresponding region of interest of the target object, map to generate an elastic map, and superimpose and fuse the elastic map containing elastic distribution data to the ultrasonic image and display it synchronously. The control unit is also used to control the low-frequency vibrator to send shear waves to the target object according to the distribution coordinates of the sampling points, and send ultra-high frame rate ultrasound signals to the distribution coordinates of the sampling points with the ultrasonic transducer array elements of the probe, and receive RF signals fed back by the distribution coordinates of the sampling points; and transmit the RF signal obtained by the probe and its distribution data to the processing unit;

the processing unit is also used to calculate the corresponding elastic feature parameters according to the received RF signal of each coordinate and its distribution data, establish a single dimensional or multi-dimensional state elastic map, and fuse the corresponding map with the ultrasonic image.

The probe 20 includes: an ultrasonic probe 21 and a low-frequency vibrator 22 that is coupled with the ultrasonic probe. The ultrasonic probe is used to transmit ultrasonic waves to the target object and receive echoes from the target object to obtain ultrasonic images. The ultrasonic probe is also used to receive RF signals fed back from the distribution coordinates of the sampling points of the target object. The low-frequency vibrator is used to transmit mechanical vibration to the target object to generate shear waves. The low-frequency vibrator 22 is used to generate mechanical shear wave transmitted to the liver through the body surface, with the central frequency between 10 Hz and 1000 Hz. Preferably, the rib space on the body surface is selected as the position for liver elasticity detection. The low-frequency vibrator 22 is coupled with the ultrasonic probe 21 on the same line perpendicular to the array of transducer array elements. The ultrasonic probe 21 acts as a vibration source of mechanical shear waves and is also a detection head for elastic measurement. The ultrasonic probe 21 is arranged by several ultrasonic piezoelectric transducer array elements in a linear, convex or two-dimensional array. Preferably, the ultrasonic piezoelectric transducers are arranged in a linear array. The ultrasonic probe 21 operates in two common ultrasonic modes. The first is B-mode ultrasonic imaging mode: the ultrasonic beam performs mechanical or electronic scanning at a frame rate of about 10 to 100 frames per second, and constructs a B-mode ultrasonic image through the image processing unit 32*a* in the main control unit 30. In general, its B-mode ultrasonic image can be obtained by linear scanning or phase control scanning. The extracted histomorphology information can be used for diagnosis and guidance for the location of the detected site. The second is the ultra-high frame rate A-mode ultrasonic acquisition mode: use delay elements to control the selected transducer array elements to output ultra-high frame rate ultrasound signals (at least 1000 frames/s) and receive radio frequency (RF) signals at the same time or in a certain time sequence, so as to track the propagation of shear waves within the target range, so as to observe the small displacement of liver tissues exposed to low-frequency shear waves.

The main control unit 30 comprises a control unit 31, a processing unit 32 and a storage unit 33. The control unit 31 is respectively connected with the image acquiring unit 10, the probe 20 and the processing unit 32, and the processing unit 32 is connected with the storage unit 33. The control unit 31 is used to receive the ultrasonic image of the image acquiring unit 10 and transmit the ultrasonic image to the processing unit 32; the processing unit 32 is used to determine the distribution coordinates of the sampling points in the region of interest according to the ultrasonic image, and transmit the distribution coordinate information of the sampling points to the control unit 31; the control unit 31 is also used to control the low-frequency vibrator to send shear waves to the target object according to the distribution coordinates of the sampling points, and send ultra-high frame rate ultrasound signals to the distribution coordinates of the sampling points with the ultrasonic transducer array elements of the probe 20, and receive RF signals fed back by the distribution coordinates of the sampling points; and transmit the RF signal obtained by the probe 20 and its distribution data to the processing unit 32; the processing unit 32 is also used to calculate the corresponding elastic feature parameters according to the received RF signal of each coordinate and its distribution data, establish a single dimensional or multi-dimensional state elastic map, and fuse the corresponding map with the ultrasonic image; the fused image is synchronously displayed by a display unit 40 connected with the processing unit 32.

The control unit 31 is for controlling the functional activities and data transmission of each component. It should be noted that the work content of the control unit 31 also includes generating specific delay timing pulses through delay elements, acting on different transducer arrays to control their timing triggering and collecting RF signals of the region of interest. The processing unit 32 mainly comprises an image processing unit 32*a*, an elasticity processing unit 32*b*, and an image and elastic parameter reconstruction unit 32*c*. The image processing unit 32*a* can generate a B-mode ultrasonic image containing histomorphology information; the elasticity processing unit 32*b* can analyze the RF signal of the echo and calculate the shear wave propagation velocity, which can be converted into the liver biological parameters related to the elastic features at the target location; the work contents of the image and elastic parameter reconstruction unit 32*c* include: 1) mapping the elastic feature parameters to a single value distribution image using a single value mapping, and mapping the elastic feature parameters to grayscale or color images using a color mapping to form a one-dimensional or two-dimensional elastic mapping map; 2) synthesizing a plurality of two-dimensional mapping maps into three-dimensional mapping maps; 3) realizing the fusion processing of the B-mode ultrasonic images (describing the morphological feature information of liver tissue) and the elastic map (describing the elastic feature information of liver tissue, etc.). The storage unit 33 includes software execution code and algorithm program.

The display unit 40 is used to display the constructed B-mode ultrasonic image, transient M-mode image and measurement results, including elastic mapping map, etc. It can also be used as a medium for interaction with users to obtain user operation instructions. The input of the display unit 40 is connected with the output of the main control unit 30, and a personal computer can be used as a carrier or it can be integrated with the main control unit 30. The data transmission mode can be wireless or wired, not limited to Bluetooth, WiFi, cable, pluggable USB cable, etc.

Figure 3:
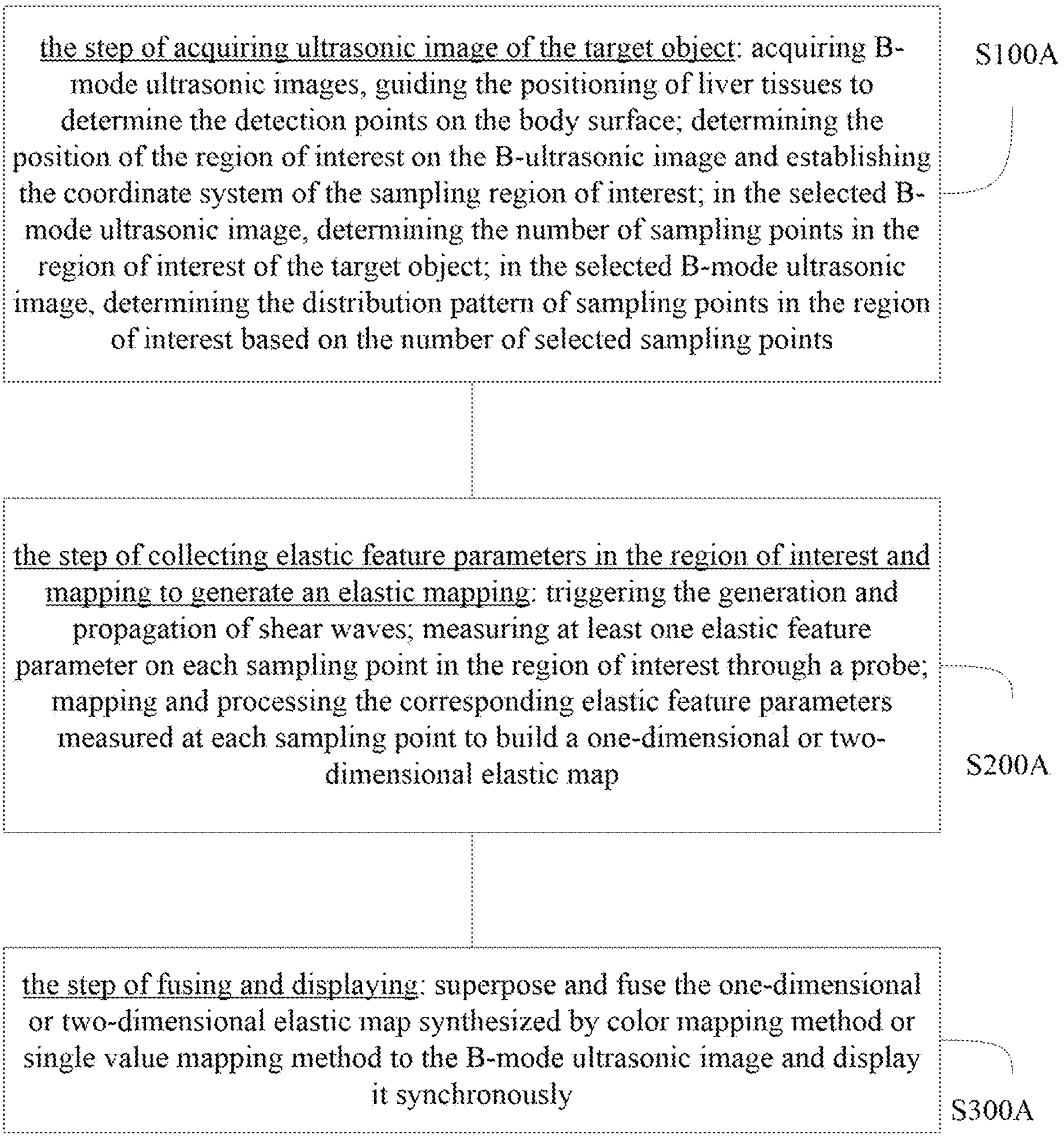
FIG. 3 is the flow diagram of one-dimensional and two-dimensional ultrasonic transient elasticity detection provided by the first embodiment of the present application.

Specifically, refer to FIG. 3 to introduce the processing steps of one-dimensional and two-dimensional ultrasonic transient elasticity detection. The main work flow is as follows;

S100A. the step of acquiring ultrasonic image of the target object: acquiring B-mode ultrasonic images, guiding the positioning of liver tissues to determine the detection points on the body surface; determining the position of the region of interest on the B-ultrasonic image and establishing the coordinate system of the sampling region of interest; in the selected B-mode ultrasonic image, determining the number of sampling points in the region of interest of the target object; in the selected B-mode ultrasonic image, determining the distribution pattern of sampling points in the region of interest based on the number of selected sampling points.

The ultrasonic probe 21 scans the imaging section with the ultrasound beam, and provides the B-mode ultrasound section image used by the image processing unit 32*a* to construct the liver tissue. Using the real-time guidance of biological tissue anatomical structure information, the placement position and angle of probe 20 are manually adjusted or automatically determined to determine the optimal measurement field of vision (FOV).

S200A. the step of collecting elastic feature parameters in the region of interest and mapping to generate an elastic mapping: triggering the generation and propagation of shear waves; measuring at least one elastic feature parameter on each sampling point in the region of interest through a probe; mapping and processing the corresponding elastic feature parameters measured at each sampling point to build a one-dimensional or two-dimensional elastic map.

In the selected B-mode ultrasonic image, determining the number of sampling points K in the region of interest (ROI): the region of interest can be a coordinate system in the direction of a single axis straight line (N), a two-dimensional plane (NM), or a three-dimensional space (NML). With respect to the direction of the straight line and two-dimensional plane, it should be understood that they are parallel to the imaging section of the B-mode ultrasonic image, that is, the ultrasonic propagation direction; as for three-dimensional space, it should be understood that it is composed of several two-dimensional regions of interest.

In the selected B-mode ultrasonic image, based on the number of selected sampling points, determining the distribution pattern of sampling points: with respect to the dimension of the coordinate system of the region of interest, the coordinates of the sampling points can be $X_n$ ($N_n$), where $1 \le n \le K$; $X_{nm}$ ($N_n$, $M_m$), where $1 \le n, m \le K$; $X_{nml}$ ($N_n$, $M_m$, $L_l$), where $1 \le n, m, l \le K$. The distribution pattern is understood as the location layout of each sampling point in the coordinate system.

The basic principle of triggering the generation and propagation of shear wave is to apply an internal (self-generated) or external excitation to the liver tissue, which can be in the form of dynamic, static and quasi-static. Preferably, the external dynamic excitation is adopted as the excitation mode: the classical implementation mode is to apply mechanical vibration on the body surface through the low-frequency vibrator 22, trigger the low-frequency shear wave to propagate in the biological tissue, and the tissue will respond accordingly according to its own physical characteristics, including displacement, strain, shear wave velocity, etc. The external vibration excitation is continuously applied at a certain repetition rate. The present application does not limit the range of the repetition rate of the vibration, and its specific embodiment includes: 1. when the shear wave generated by the current vibration is still propagating in the biological tissue, the next vibration will be triggered; 2. when the shear wave generated by the current vibration stops propagating in the biological tissue, the next vibration will be triggered; 3. after the shear wave generated by the current vibration stops propagating in the biological tissue, the next vibration will be triggered at a specific time interval. When a plurality of shear waves generated in the biological tissue by continuous vibration propagate, the ultra-high frame rate ultrasound will simultaneously track these shear waves. Other non-limiting embodiments can be the acoustic radiation force generated by vibration, compression, impact and focused ultrasound excited in vitro or in vivo (heart beat or respiratory movement).

Measuring at least one parameter on each sampling point in the region of interest, and performing multi-point measurement on the sampling points in the selected coordinate system: different transducer array element subsets transmit ultra-high frame rate ultrasound signals to each sampling point at a specific time sequence, and then obtain RF signals reflected back by the corresponding liver tissue. In order to characterize the response of the biological tissue surface after being stimulated by external vibration, the specific embodiment can be: analyze the RF echo information of each sampling point through the elasticity processing unit 32*b*, and calculate the biomechanical parameters; classically, the elastic inherent value: Young's modulus is derived.

$$E=3\rho v^2$$

Where E is Young's modulus.

Biomechanical parameters describe the mechanical and physical properties related to tissue elasticity in a non-restrictive way, including Young's modulus, shear wave velocity, shear wave attenuation coefficient, Poisson's ratio, shear modulus, bulk modulus, etc.

Other non-limiting feature parameters can be ultrasonic parameters and B-ultrasound image feature parameters. The ultrasonic parameters in liver tissue can be ultrasonic velocity, ultrasonic attenuation, ultrasonic backscatter coefficient, etc. in a non-restrictive way. The expression of ultrasonic propagation in tissues can be expressed as:

$$I_d = I_0 e^{-\alpha d}$$

Wherein, $I_0$ represents the ultrasonic strength at the initial position, $I_d$ represents the ultrasonic strength at the propagation distance d, and represents the ultrasonic attenuation coefficient.

In a non-restrictive way, the feature parameters of B-ultrasound images are understood as color features, texture features, shape features, spatial relationship features, etc. The most common implementation is the statistics of texture feature parameters extracted by certain digital image processing techniques, that is, the gray distribution function of image local properties. Texture analysis methods can include statistical analysis methods, structural analysis methods, signal processing methods, model methods, etc.

S300A. the step of fusing and displaying: superpose and fuse the one-dimensional or two-dimensional elastic map synthesized by color mapping method or single value mapping method to the B-mode ultrasonic image and display it synchronously.

Figure 4:
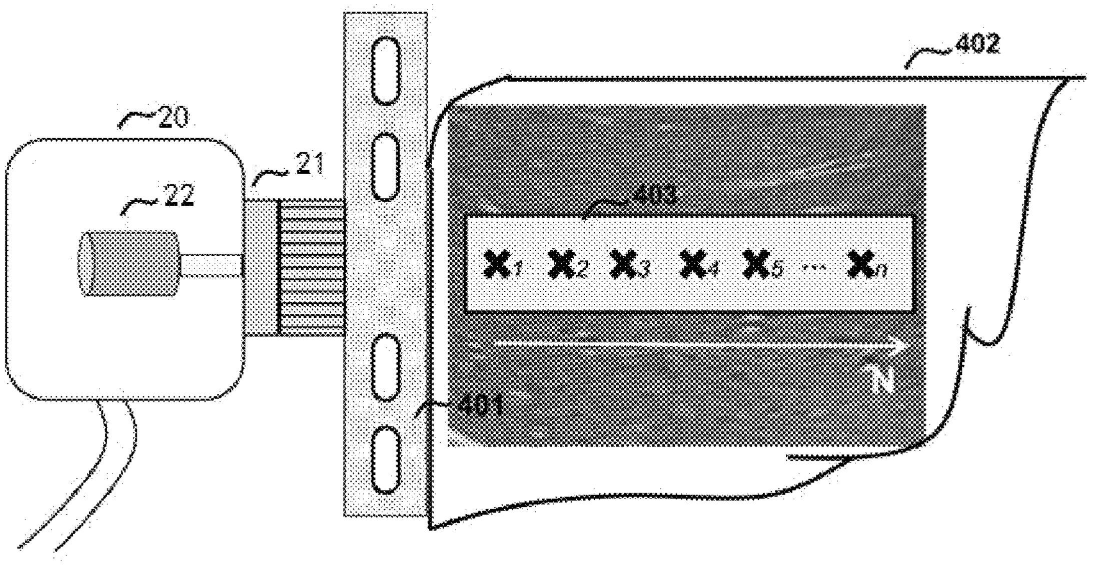
FIG. 4 is a schematic diagram of the one-dimensional elastic detection method of the liver provided by the first embodiment of the present application.

Further referring to the schematic diagram of the elasticity one-dimensional detection method of the liver provided in FIG. 4, the probe 20 composed of the linear array ultrasonic probe 32 is placed on the body surface skin outside the rib space 401, and the measured liver tissue 402 is located on the opposite side of the contact surface. The longitudinal depth direction (i.e. linear coordinate system) in the region of interest 403 contains n sampling points, namely $X_1$, $X_2$, $X_3$, . . . Xn (n=1,2,3, . . . , n≥1). Generally, the longitudinal depth N refers to the direction along which the ultrasonic wave travels. It is worth noting that the present application does not limit the specific number of sampling points and the distribution spacing in the one-dimensional direction.

Figure 5:
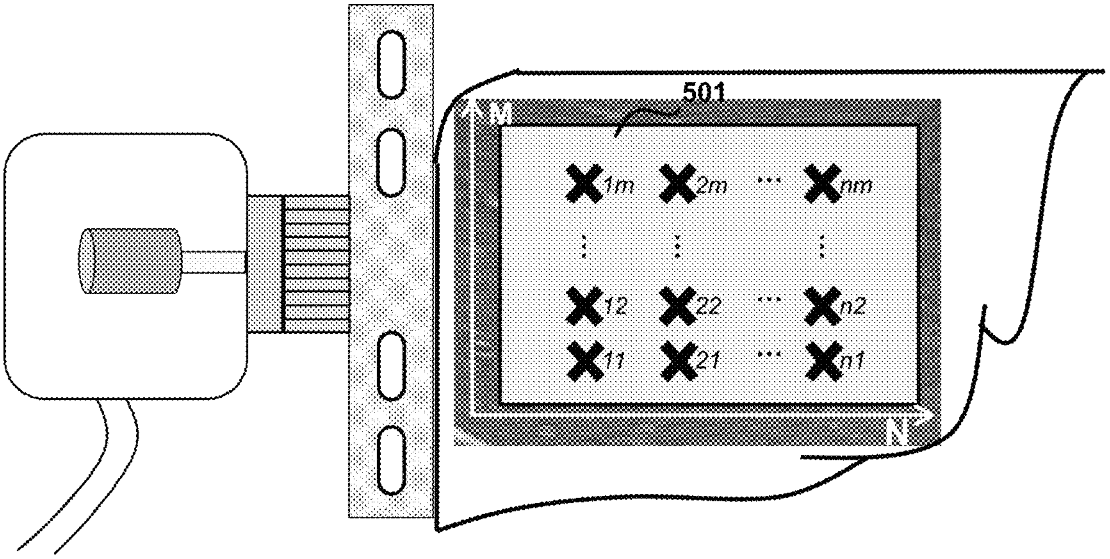
FIG. 5 is a schematic diagram of the two-dimensional elastic detection method of the liver provided by the first embodiment of the present application.

Further refer to the schematic diagram of the elasticity two-dimensional detection method of the liver provided in FIG. 5, and the region of interest 501 (i.e. plane rectangular coordinate system) contains n×m sampling points, namely $X_{11}$, $X_{12}$, $X_{23}$, . . . $X_{nm}$ (n=1,2,3, . . . , n≥1; m=1,2,3, . . . , m≥1), which are arranged in a rectangular array. Generally, the plane of the region of interest 501 has two direction axes, namely, the longitudinal depth N and the transverse length M. The transverse length refers to the direction perpendicular to the ultrasonic propagation direction. It is worth noting that the present application does not limit the specific number of sampling points and their layout pattern in the two-dimensional direction.

Steps of processing after the superposition and fusion and displaying of measurement results: in order to visualize the one-dimensional distribution state, the corresponding parameters $y_1$, $y_2$, $y_3$, . . . $y_n$ (n=1,2,3, . . . , n≥1) measured at each sampling point, namely $X_1$, $X_2$, $X_3$, $X_n$ (n=1, 2,3, . . . , n≥1) are processed. In order to visualize the two-dimensional distribution state, the corresponding parameters $y_{11}$, $y_{12}$, $y_{23}$, . . . $y_{nm}$ (n=1,2,3, . . . , n≥1; m=1, 2,3, . . . , m≥1) measured at each sampling point, namely $X_{11}$, $X_{12}$, $X_{23}$, . . . $X_{nm}$ (n=1,2,3, . . . , n≥1; m=1,2,3, . . . , m≥1) are processed. A typical application is to map the elastic feature parameter value to the image, which is represented by color coding or scalar (specific value) and displayed by the display unit 40. An embodiment may be providing an image and elastic parameters reconstruction unit 32*c* that constructs a map (expressed in color or gray scale) by interpolation, fitting and other mathematical processing methods. Preferably, the two-dimensional/three-dimensional elastic map is displayed and superimposed and fused in the B-mode ultrasonic image. The elastic mapping map uses color coded grayscale or color images to represent the elastic feature information, maps the elastic strength of the liver at specific spatial locations to the images at corresponding locations one by one, and uses different colors or grayscales to represent the elastic distribution. On the other hand, the elastic map is also equipped with a scale bar to explain the strength value coding of the elastic map through color gradient and reading range. It should be noted that the result of fusion display is that morphological feature information and elastic feature information are displayed in the same image at the same time. In order to quantify the degree of liver fibrosis and improve the reliability of the results of a single detection, taking the above-mentioned one-dimensional elasticity detection method as an example, the result Z can be expressed by the mean value calculated by the formula: $Z=(y_1+y_2+y_3+ \ldots +y_n)/n$. Without limitation, the result Z can also be the calculated value obtained by other mathematical statistics methods, including median, variance, quartile, normal distribution, etc.

Figure 6:
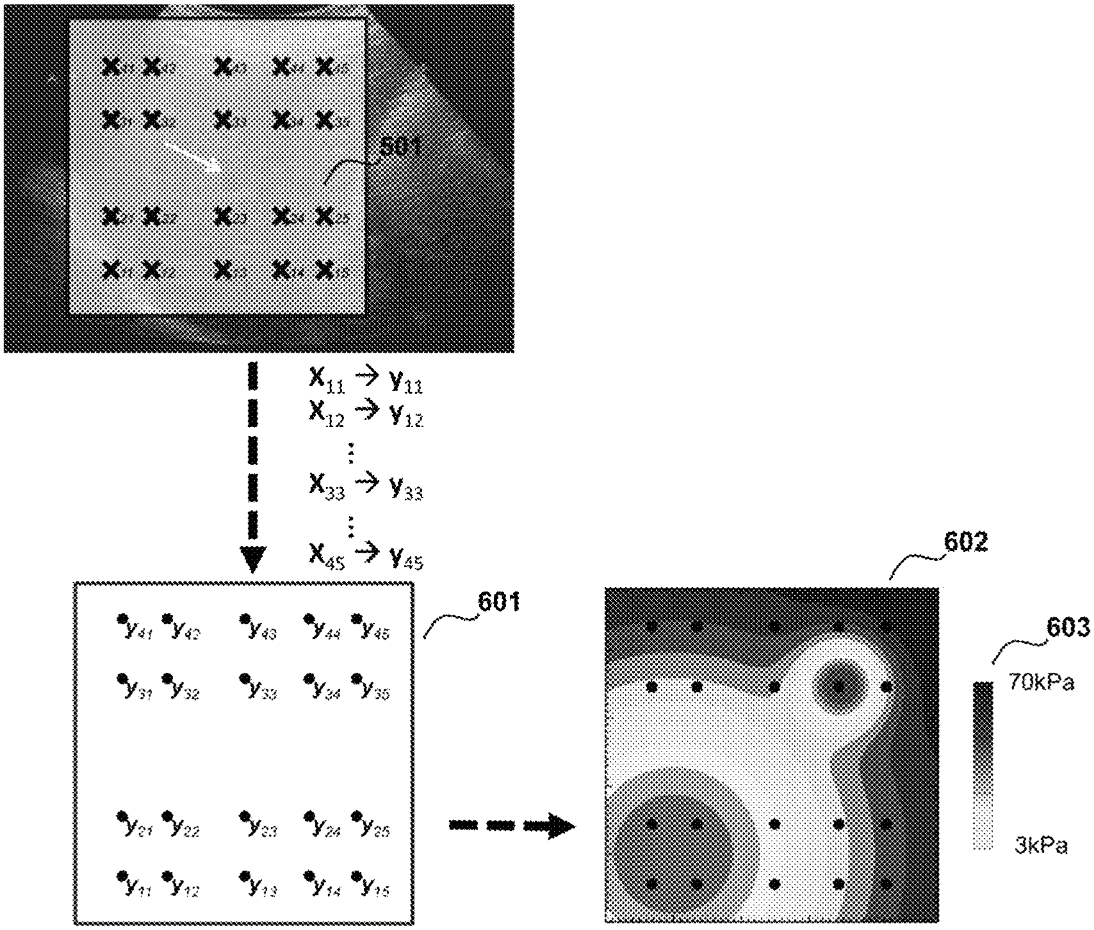
FIG. 6 is an example diagram of the synthesis of the two-dimensional map provided by the first embodiment of the present application.

Further, refer to FIG. 6, which shows an example of the implementation of composing a two-dimensional map. The plane of the region of interest 501 includes several sampling points arranged in a custom pattern. It is worth noting that the principle of sampling point placement is to avoid non-liver parenchymal tissues (such as intrahepatic vessels, bile ducts and ligaments). The white arrow points to the intrahepatic vessels. The elastic parameters ($y_{11}$ to $y_{45}$) measured at each sampling point ($X_{11}$ to $X_{45}$) include the following information: Young's modulus (indicating the value size) and location information (indicating the spatial distribution), forming a single value mapping map 601. A two-dimensional elastic grayscale map 602 is generated by mapping coding technology, and a scale bar 603 is provided for interpretation.

Further refer to FIG. 7, showing the flow diagram of three-dimensional ultrasonic transient elasticity detection; the following steps are included:

S100B. the step of acquiring ultrasonic image of the target object: acquiring B-mode ultrasonic images, guiding the positioning of liver tissues; in the selected B-mode ultrasonic image, determining the number of sampling points in the region of interest of the target object; in the selected B-mode ultrasonic image, determining the distribution pattern of sampling points in the region of interest based on the number of selected sampling points.

S200B. the steps of collecting 3D data and mapping to generate 3D elastic mapping: triggering the generation and propagation of shear waves; measuring multiple elastic feature parameters on each sampling point including longitudinal depth, transverse length and thickness in the region of interest; post-processing the corresponding elastic feature parameters measured at each sampling point, and constructing a three-dimensional elastic mapping map by interpolation, fitting and other mathematical processing methods for the processed elastic feature parameters.

S300B. the steps of fusing and displaying: superpose and fuse the elastic map containing three-dimensional elastic distribution data into the B-mode ultrasonic image and display it synchronously.

Figure 8:
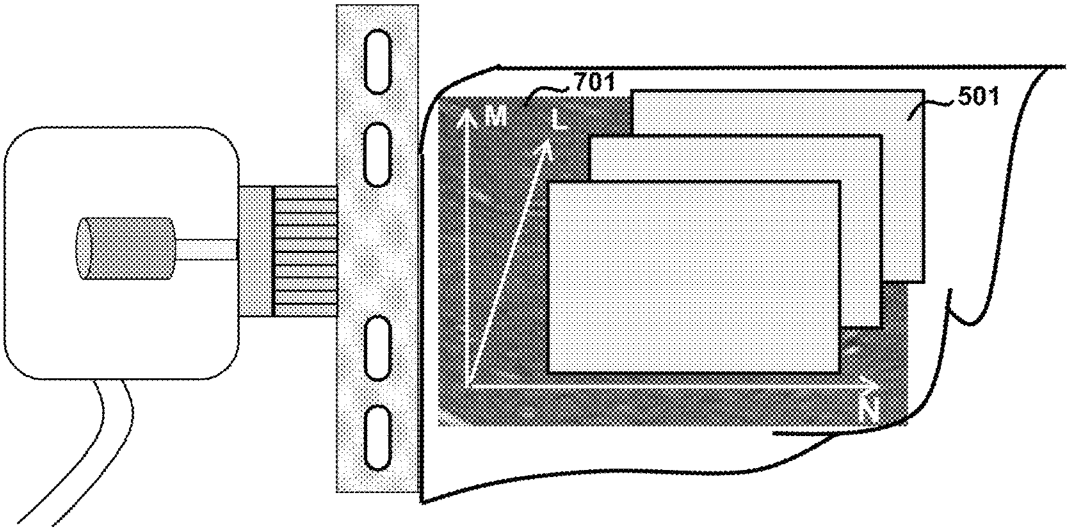
FIG. 8 is a schematic diagram of the three-dimensional elastic detection method of the liver provided by the first embodiment of the present application.

In combination with the specific embodiment of collecting 3D elastic distribution shown in FIG. 8, it is established that the region of interest 701 is a 3D spatial coordinate system. The region of interest 701 has three direction axes, namely, longitudinal depth N, transverse length M and thickness L. In the space of the region of interest 701, there are several two-dimensional planes of the region of interest

501 along the direction of thickness L, which contains several sampling points, namely $X_{111}$, $X_{121}$, $X_{123}$, . . . $X_{nml}$ (n=1,2,3, . . . , n>=1; m=1,2,3, . . . , m>=1; 1=1,2,3, . . . , 1>=1). The thickness L refers to an independent direction dimension that is not parallel to the longitudinal depth N and the transverse length M. The data sampling in the direction of thickness L can be realized by two kinds of ultrasonic probes 208. In the first case, the linear array probe, phased array probe and convex array probe of the transducer array elements arranged in the same plane are used in the following two specific ways. The first method is multi-point detection in the rib space: the probe 20 is moved from left to right or from right to left along the direction of the thickness L in a selected rib space, and a group of above-mentioned two-dimensional measurements are carried out on different spatial sections of the liver parenchyma in turn; the second method is multi-point detection between rib spaces: move the probe 20 from top to bottom or from bottom to top to the next adjacent rib space, and conduct a group of above-mentioned two-dimensional measurements on different spatial sections of the liver parenchyma in turn. Please note that the protection scope of the present application does not limit the specific detection times in each group, which should be understood as at least>2 times/group, the more is better.

In the second case, a two-dimensional matrix probe is used to place it at a certain detection position in the rib space to collect three-dimensional data in a small range. Generally, the direction of the thickness L refers to the arrangement of transducer array elements in the width direction. Or the above multi-point detection method is used to collect 3D data in a large range.

Synthesis of three-dimensional data: the typical application is to provide the image and elastic parameter reconstruction unit 32*c*, and synthesize the two-dimensional elastic map into the three-dimensional elastic map through interpolation, fitting and other mathematical processing methods, so as to explain the distribution of elastic features in three-dimensional space.

Further, in order to generate directional ultra-high frame rate ultrasound signals and execute the above sampling mode, the present application can be realized by two technical solutions: calculate the time delay (time delay) of transmitting and receiving ultrasonic waves of corresponding transducer array elements according to the coordinate position of the target sampling point; a. single-dimension measurement: obtain the radio frequency (RF) signal by stimulating a single array element; based on the RF signal and controlling the time delay, the sampling in the longitudinal detection depth is realized; b. multi-dimensional space measurement: simultaneously or with mutual delay, obtain radio frequency (RF) signals by controlling different array elements in parallel; based on RF signals and time delay control, sampling in two-dimensional space (i.e. longitudinal depth and transverse length) or three-dimensional space is completed; multiple elastic feature parameters can be measured in an imaging section on the same surface detection point.

The present application also provides a computer-readable storage medium, in which a computer program is stored in the storage unit 33, including software execution code and algorithm program. When the software execution code and algorithm program are executed by the processor in the process of elasticity dimensional detection of biological tissues, the processor is allowed to execute one-dimensional, two-dimensional and three-dimensional ultrasonic transient elastic detection steps: acquiring the two-dimensional ultrasonic image, determining the position of the region of interest on the two-dimensional ultrasonic image; and establishing the sampling coordinate system of the corresponding dimension in the region of interest, and determining the number of and coordinate position of the sampling points in the selected corresponding dimension sampling coordinate system; measuring at least one elastic feature parameter on each selected sampling point in the region of interest through a probe; mapping and processing corresponding elastic feature parameters measured at each sampling point to construct an elastic map of the sampling coordinate system of the corresponding dimension; superimposing and fusing the elastic map of corresponding dimensions to the two-dimensional ultrasonic image and displaying it simultaneously. Further, triggering the probe to transmit directional ultra-high frame rate ultrasound signal to track the shear wave for sampling, and calculating the time delay of transmitting and receiving the ultrasonic wave for corresponding array elements in the transducer array before sampling; the sampling mode includes: obtaining a radio frequency (RF) signal by stimulating a single array element of the probe, and calculating the elastic feature parameters at a designated position in a single dimensional space; or obtaining the radio frequency (RF) signal by controlling different array elements of the probe in parallel, and calculating the elastic feature parameters at the designated position in the multi-dimensional space.

It should be noted that the biological tissue elasticity dimensional detection method, system and storage medium belong to the same inventive concept. Those skilled in the art can understand that the realization of all or part of the processes in the methods of the above embodiments can be accomplished by instructing relevant hardware through a computer program. The program can be stored in a non-volatile computer readable storage medium. When the program is executed, it can include the processes of the embodiments of the above methods. Among them, any reference to memory, storage, database or other media used in the embodiments provided in the application can include non-volatile and/or volatile memory. Non-volatile memory can include read-only memory (ROM), programmable ROM (PROM), electrically programmable ROM (EPROM), electrically erasable programmable ROM (EEPROM), or flash memory. Volatile memory may include random access memory (RAM) or external cache memory. As an illustration, RAM is available in many forms, such as static RAM (SRAM), dynamic RAM (DRAM), synchronous DRAM (SDRAM), dual data rate SDRAM (DDRSDRAM), enhanced SDRAM (ESDRAM), synchronous link DRAM (SLDRAM), memory bus direct RAM (RDRAM), direct memory bus dynamic RAM (DRDRAM), and memory bus dynamic RAM (RDRAM). The serial number of the embodiments of the present application is only for description and does not represent the advantages and disadvantages of the embodiments.

To sum up, in the present application, the ultrasonic transducer is used to transmit ultrasound and receive the echo signal reflected by the liver to obtain the ultrasonic image of the liver; the coordinate system of the sampling region of interest is established, and the number and coordinate distribution of the sampling points is determined; the ultrasonic probe formed by several ultrasonic piezoelectric transducer arrays in linear array, convex array or two-dimensional array is used to realize elasticity dimensional measurement, which can quickly and accurately obtain one-dimensional, two-dimensional and three-dimensional elastic distribution of the liver, improve the inspection efficiency and increase the reliability of the results. In particular, for one-dimensional and two-dimensional elastic measurement, the present application can realize multiple sampling (that is, multiple elastic feature parameters can be measured simultaneously) at a detection point without manually moving the position of the probe, and synthesize a single value or colored elastic mapping distribution map, overcoming the limitations of single value transient elastic measurement technology in the prior art that it can only realize a single sample at one time and cannot obtain spatial distribution information; the time is saved, the inspection efficiency is improved, the system error is minimized by increasing the sample size, the reliability of the results is improved, and the sampling error is reduced; an adjustable and switchable sampling point distribution mode is provided by the present application, which can selectively avoid the large blood vessels and bile duct system, obtain the distribution status of biological parameters of the liver biological tissues, and make the results more accurate and customized.

The above is only a preferred embodiment of the present application, and is not intended to limit the present application. Any modification, equivalent replacement, improvement, etc. made within the spirit and principle of the present application shall be included in the protection scope of the present application.

What is claimed is:

1. An elasticity dimensional detection method for biological tissue detection, wherein, the method comprises the following steps:

acquiring an ultrasonic image of a target object;

in response to an external vibration excitation, collecting elastic feature parameters at a designated coordinate position of the target object, and mapping to generate an elastic map; and superimposing and fusing the elastic map containing elastic distribution data to the ultrasonic image and simultaneously displaying;

the step of in response to the external vibration excitation, collecting elastic feature parameters at the designated coordinate position of the target object, and mapping to generate the elastic map comprises:

based on the ultrasonic image, establishing a coordinate system of a sampling region of interest at a single detection point on the body surface, and determining the number of sampling points and coordinate distribution positions thereof; the sampling region of interest is located in the ultrasonic image and is one of the coordinate systems of two-dimensional plane or three-dimensional space; based on the coordinate system dimension and position of the sampling region of interest, the sampling points are specific coordinate points located in the coordinate system, which are distributed according to a customizable distribution pattern that selectively avoids intrahepatic blood vessels, bile ducts and ligaments based on the anatomical structure information contained in the ultrasonic image;

measuring elastic feature parameters of the sampling points of the target object, the step of measuring elastic feature parameters further comprises: stimulating a probe that is coupled to a low-frequency vibrator to apply, via the low-frequency vibrator coupled to the probe, low-frequency mechanical vibration on a body surface to generate a shear wave to propagate in a depth direction in the biological tissue; controlling the array elements in the ultrasonic transducer array to transmit and receive an ultra-high frame rate ultrasonic signal of at least 1000 frames per second to track the shear wave along the designated coordinate position or different directions of each sampling point, and simultaneously performing parameter measurements on multiple sampling points located within a single image plane acquired without repositioning the probe, by controlling different array elements of the probe in parallel; and mapping to generate the elastic map, the step of mapping to generate the elastic map further comprises: using mapping technology to encode the elastic feature parameters at the designated coordinate position into single value mapping or color mapping to represent the distribution state of elastic features;

triggering the probe to transmit directional ultra-high frame rate ultrasonic signal to track the shear wave for sampling;

the sampling mode includes: obtaining a radio frequency (RF) signal by stimulating a single array element of the probe, and calculating the elastic feature parameters at a designated position in a single dimensional space; or simultaneously obtaining the radio frequency (RF) signal by controlling different array elements of the probe in parallel to acquire RF signals corresponding to the multiple sampling points in a single acquisition, and calculating the elastic feature parameters at the designated position in a multi-dimensional space;

the external vibration excitation is continuously applied at a certain repetition rate via the low-frequency vibrator coupled to the probe, and the ultra-high frame rate ultrasonic signal acquired in a single continuous acquisition simultaneously tracks the propagation of a plurality of multiple shear waves that are concurrently present in the biological tissue as a result of said continuous vibration at said repetition rate.

2. The detection method according to claim 1, wherein, the elastic feature parameters are parameters related to the elasticity of biological tissues, including elastic parameters expressed by Young's modulus, ultrasonic parameters, and two-dimensional ultrasonic image feature parameters.

3. The detection method according to claim 2, further comprising calculating the time delay of transmitting and receiving the ultrasonic signal for corresponding array elements in the transducer array before sampling.

4. The detection method according to claim 2, wherein, the collecting of the ultra-high frame rate ultrasonic signal is carried out simultaneously with respect to at least two positions or directions.

5. The detection method according to claim 1, wherein, collecting of three-dimensional data of three-dimensional ultrasonic transient elasticity detection is realized by single point detection in which the ultrasonic probe, which in this case is a two-dimensional array probe is fixedly placed on a single detection point on the body surface such that data at a plurality of sampling points distributed in three-dimensional space are acquired without physical movement of the probe; or by multi-point detection in which the ultrasonic probe, which in this case is a linear probe, a phased probe or a convex array probe are moved on multiple detection points on the body surface.

6. An elasticity dimensional detection system for biological tissue detection, comprises an image acquiring unit for acquiring an ultrasonic image of a target object and a probe for transmitting and receiving an ultrasonic wave signal; wherein, the detection system further comprises:

a main control unit, respectively connected with the image acquiring unit and the probe, is used to acquire the ultrasonic image of the target object from the image acquiring unit, establish a coordinate system of a sampling region of interest of a corresponding dimension based on the acquired ultrasonic image at a single detection point on the body surface, and determine a number of sampling points and coordinate distribution positions thereof such that the sampling points are distributed according to a customizable distribution pattern that selectively avoids intrahepatic blood vessels, bile ducts and ligaments identified from anatomical structure information in the ultrasonic image; receive the elastic feature parameters of the corresponding region of interest of the target object, map to generate an elastic map, and superimpose and fuse the elastic map containing elastic distribution data to the ultrasonic image and display it synchronously;

the probe comprises an ultrasonic probe and a low-frequency vibrator mechanically coupled with the ultrasonic probe on a same line perpendicular to an array of transducer array elements, such that the low-frequency vibrator and the ultrasonic probe are both applied at the same body surface location; the ultrasonic probe is arranged by several ultrasonic piezoelectric transducer array elements in a linear, convex or two-dimensional array; the low-frequency vibrator continuously applies mechanical vibration on a body surface at a certain repetition rate via said mechanical coupling to the ultrasonic probe to generate a plurality of shear waves propagated in biological tissues by continuous vibration such that the plurality of shear waves are concurrently present in the biological tissue;

the main control unit comprises a control unit and a processing unit, the control unit is respectively connected with the image acquiring unit, the probe and the processing unit, the control unit is used to receive the ultrasonic image from the image acquiring unit and transmit the ultrasonic image to the processing unit; the processing unit is used to determine the distribution coordinates of the sampling points in the region of interest according to the ultrasonic image based on the anatomical structure information contained therein to avoid non-liver parenchymal tissues, and transmit the distribution coordinate information of the sampling points to the control unit;

the control unit is also used to control a low-frequency vibrator that is coupled to the ultrasonic probe to send shear waves to the target object according to the distribution coordinates of the sampling points, and send ultra-high frame rate ultrasound signals of at least 1000 frames per second to the distribution coordinates of the sampling points by controlling different ones of the ultrasonic transducer array elements of the probe in parallel, so as to acquire RF signals corresponding to the plurality of sampling points simultaneously within a single acquisition, and receive RF signals fed back by the distribution coordinates of the sampling points; and transmit the RF signal obtained by the probe and its distribution data to the processing unit;

the processing unit is also used to calculate the corresponding elastic feature parameters according to the received RF signal of each coordinate and its distribution data, the processing unit further configured to simultaneously track propagation of the plurality of shear waves concurrently present in the biological tissue using the ultra-high frame rate RF signals acquired in said single acquisition, establish a single dimensional or multi-dimensional state elastic map, and fuse the corresponding map with the ultrasonic image;

the fused image is synchronously displayed by a display unit connected with the processing unit.

7. A non-transitory computer-readable storage medium, wherein, comprises a storage unit storing computer programs, when the computer programs are executed by a central processing unit (CPU) in a main control unit, the steps of the detection method according to claim 1 is realized.

* * * * *